(12) United States Patent
Kadota

(10) Patent No.: US 7,748,271 B2
(45) Date of Patent: Jul. 6, 2010

(54) APPARATUS AND METHOD FOR RESISTANCE-BASED MUSCULAR FORCE EVALUATION USING A HEXAGONAL DIAGRAM OF OUTPUT DISTRIBUTION

(75) Inventor: Kenji Kadota, Gunma (JP)

(73) Assignee: OKI Electric Industry Co., Ltd., Tokyo (JP)

( * ) Notice: Subject to any disclaimer, the term of this patent is extended or adjusted under 35 U.S.C. 154(b) by 100 days.

(21) Appl. No.: 12/039,339

(22) Filed: Feb. 28, 2008

(65) Prior Publication Data

US 2008/0202232 A1 Aug. 28, 2008

(30) Foreign Application Priority Data

Feb. 28, 2007 (JP) .............................. 2007-048511

(51) Int. Cl.
*A61B 5/22* (2006.01)
(52) U.S. Cl. .................................................. 73/379.01
(58) Field of Classification Search ............. 73/379.01, 73/379.02; 623/25; D21/191
See application file for complete search history.

(56) References Cited

U.S. PATENT DOCUMENTS

| | | | | |
|---|---|---|---|---|
| 4,702,108 A | * | 10/1987 | Amundsen et al. | 73/379.01 |
| 4,805,455 A | * | 2/1989 | DelGiorno et al. | 73/379.01 |
| 5,002,269 A | * | 3/1991 | Jones | 482/10 |
| 5,116,296 A | * | 5/1992 | Watkins et al. | 482/91 |
| D373,394 S | * | 9/1996 | Jacobs | D21/191 |
| 2008/0161937 A1 | * | 7/2008 | Sankai | 623/25 |

FOREIGN PATENT DOCUMENTS

JP 2000-210272 8/2000

OTHER PUBLICATIONS

T. Fujikawa, et al. "Functional Coordination Control of Pairs of Antagonistic Muscles", Transactions of the Japan Society of Mechanical Engineers, vol. 63, No. 607 (Mar. 1997) pp. 769-776, Treatise No. 96-1040, Abstract, referred to on p. 1 of specification.
T. Fujikawa, et al. "Coordinate Activities of a Group of Mono-articular Muscle and a Group of Bi-articular Muscles in Upper Limbs, Acting in Antagonism to One Another, and Analysis of Control Functions thereof by a Mechanical Model", Biomechanisms 13, The Society of Biomechanisms, pp. 181-191, 1996, Referred to on p. 7 of specification.

* cited by examiner

*Primary Examiner*—Jewel Thompson
(74) *Attorney, Agent, or Firm*—Rabin & Berdo, PC

(57) ABSTRACT

The torques at the first and second joints of a test subject are measured, which may be generated simultaneously by the coordinate action of the antagonistic mono- and bi-articular muscles. A hexagonal diagram of the output distribution is formulated on a plane formed by two axes corresponding to torques at the first and second joints as. Based on the diagram, the muscular force of the subject, changing through training, may accurately be evaluated, without the necessity of specifying the force of individual function-based muscles of praxis, even if the subject changes his or her position or joint angle. The torques at the first and second joints are measured, which are generated simultaneously by the coordinate action of the antagonistic mono- and bi-articular muscles. The muscular force of the bi-articular link mechanism of the subject is thus measured by the diagram.

9 Claims, 9 Drawing Sheets

APPARATUS AND METHOD FOR RESISTANCE-BASED MUSCULAR FORCE EVALUATION USING A HEXAGONAL DIAGRAM OF OUTPUT DISTRIBUTION

BACKGROUND OF THE INVENTION

1. Field of the Invention

The present invention relates to an apparatus, a method and a system for resistance-based evaluation of a muscular force.

2. Description of the Background Art

A system for resistance-based evaluation of a muscular force, exploiting a bi-articular link mechanism, such as a bi-articular arm apparatus, has been proposed in Japanese patent laid-open publication No. 2000-210272, for instance. In this known system for resistance-based evaluation of a muscular force, the muscular output of the antagonistic mono-articular muscles and the antagonistic bi-articular muscles of a test subject, or testee, whose muscular force is being evaluated, is measured with a pressure sensor. The test subject, or person, exerts the force with maximum isometric effort, at his or her four limbs, in a plurality of preset directions. Then, a hexagonal diagram showing characteristics of the output distribution is prepared to use the so prepared diagram to evaluate the force of function-based muscles of praxis.

There has also been proposed a model for bi-articular muscles that functions for a mammal inclusive of the human being to bend an arm, and researches are now underway with the use of the model to control the movements of the bi-articular link mechanism. See T. Fujikawa et al., "Functional Coordination Control of Pairs of Antagonistic Muscles", Transactions of The Japan Society of Mechanical Engineers, Vol. 63, No. 607 (1997-3) pp. 769-776, Treatise No. 96-1040. In this research, it is stated to be desirable to use, as a driving source, a model of an actuator having an elastic element and a contractile element that exerts the force in the contracting direction.

In the above-described conventional solutions for resistance-based muscular force evaluation, the four limbs of a test subject are simulated to a link system, and a muscular force is evaluated based on a hexagonal diagram plotting characteristics of output distribution. Since the hexagonally-shaped output distribution, plotted on the diagram, differs with the joint angles of the link system, measurement cannot be conducted unless proportionally contracted. Further, it is difficult to arrive at proper comparison if the test subject changes his or her position each time his or her muscular force is measured.

SUMMARY OF THE INVENTION

It is an object of the present invention to provide an apparatus for resistance-based muscular force evaluation with an improved accuracy. It is also an object of the invention to provide such a system and a method for resistance-based muscular force evaluation.

It is another object of the invention to provide an apparatus for resistance-based muscular force evaluation which can more accurately evaluate a muscular force as changed by training, without the necessity of specifying the individual muscular force of each of the function-based muscles of praxis, regardless of the position or joint angle of a test subject changing.

In accordance with the present invention, the axial torque which could simultaneously be generated at the first and second joints by a coordinate action of the antagonistic mono-articular muscles and the antagonistic bi-articular muscles are measured to formulate a hexagonal diagram plotting characteristics of the output distribution on a plane formed by a couple of axes corresponding to the axial torques at the first and second joints.

In accordance with the present invention, a resistance-based muscular force evaluation apparatus for a bi-articular link mechanism of a test subject comprises a saddle for a test subject to sit on, a robot arm adjustable to the length of an upper limb or a lower limb of the test subject and having its distal end of the robot arm exhibiting elasticity, a fastener for securing the robot arm to the upper limb or the lower limb of the test subject, a controller for controlling the torques at a first joint and at a second joint of the robot arm, and an angular sensor for sensing joint angles at the first and second joints of the robot arm. The controller exercises control so that the elasticity will vary with the direction to indicate the direction in which the test subject is to exert the force to measure his or her muscular force.

In accordance with the present invention, in a resistance-based muscular force evaluation method for a bi-articular link mechanism of a test subject, the bi-articular link mechanism includes a set of antagonistic mono-articular muscles about a first joint, another set of antagonistic mono-articular muscles about a second joint, both sets of muscles giving rise to effective movement in a plane including the first and second joints and the distal end of the mechanism, and a set of antagonistic bi-articular muscles astride the first and second joints. The method comprises: preparing a robot arm including a first link having opposite ends respectively connected to the first joint and the second joint, a second link having one end connected to the second joint and another end forming a distal end of the robot arm; measuring torques at the first joint and at the second joint which may be generated simultaneously by a coordinate action of the antagonistic mono-articular muscles and antagonistic bi-articular muscles; formulating a hexagonal diagram of output distribution on a plane formed by two axes corresponding to the torque at the first joint and the torque at the second joint; and measuring a muscular force of the bi-articular link mechanism of the test subject by the diagram.

In accordance with the present invention, in a resistance-based muscular force evaluation system for a bi-articular link mechanism of a test subject, the bi-articular link mechanism includes: a set of antagonistic mono-articular muscles about a first joint, and another set of antagonistic mono-articular muscles about a second joint, both of the sets of muscles producing an exercise movement in a plane including the first and second joints and the distal end of the mechanism; and a set of antagonistic bi-articular muscles astride the first and second joints. The system comprises: a first link having opposite ends respectively connected to the first joint and the second joint; and a second link having one end connected to the second joint and another end forming a distal end of the link mechanism. The torque at the first joint and the torque at the second joint which may be generated simultaneously by a coordinate action of the antagonistic mono-articular muscles and antagonistic bi-articular muscles are measured. A hexagonal diagram of output distribution is formulated on a plane formed by two axes corresponding to the torque at the first joint and the torque at the second joint, and a muscular force of the link mechanism of the test subject is measured by the diagram.

Further in accordance with the present invention, in a resistance-based muscular force evaluation system for a bi-articular link mechanism of a test subject, the system may comprise a saddle for the test subject to sit on, a robot arm adjustable to the length of an upper limb or a lower limb of the test subject, a fastener for securing the robot arm to the upper or lower limb of the test subject, a controller for controlling the torques at a first or second joint of the robot arm, and an angular sensor for sensing joint angles at the first and second joints of the robot arm. The torques at the first and second joints are measured when the force exerted at the distal end of the robot arm is brought into register with the force exerted by the distal end of the bi-articular link mechanism of the test subject.

Thus, according to the present invention, the values of torques at the first joint and at the second joint are measured, which are generated simultaneously by the coordinate action of the antagonistic mono-articular muscles and antagonistic bi-articular muscles. A hexagonal diagram of output distribution is formulated on a plane defined by two axes corresponding to the torque at the first joint and the torque at the second joint. The muscular force of the test subject, changed by the training, may accurately be evaluated, without the necessity of specifying the force of individual function-based muscles of praxis, even when the test subject is changed in position or joint angle.

BRIEF DESCRIPTION OF THE DRAWINGS

The objects and features of the present invention will become more apparent from consideration of the following detailed description taken in conjunction with the accompanying drawings in which.

DESCRIPTION OF THE PREFERRED EMBODIMENTS

Figure 1:
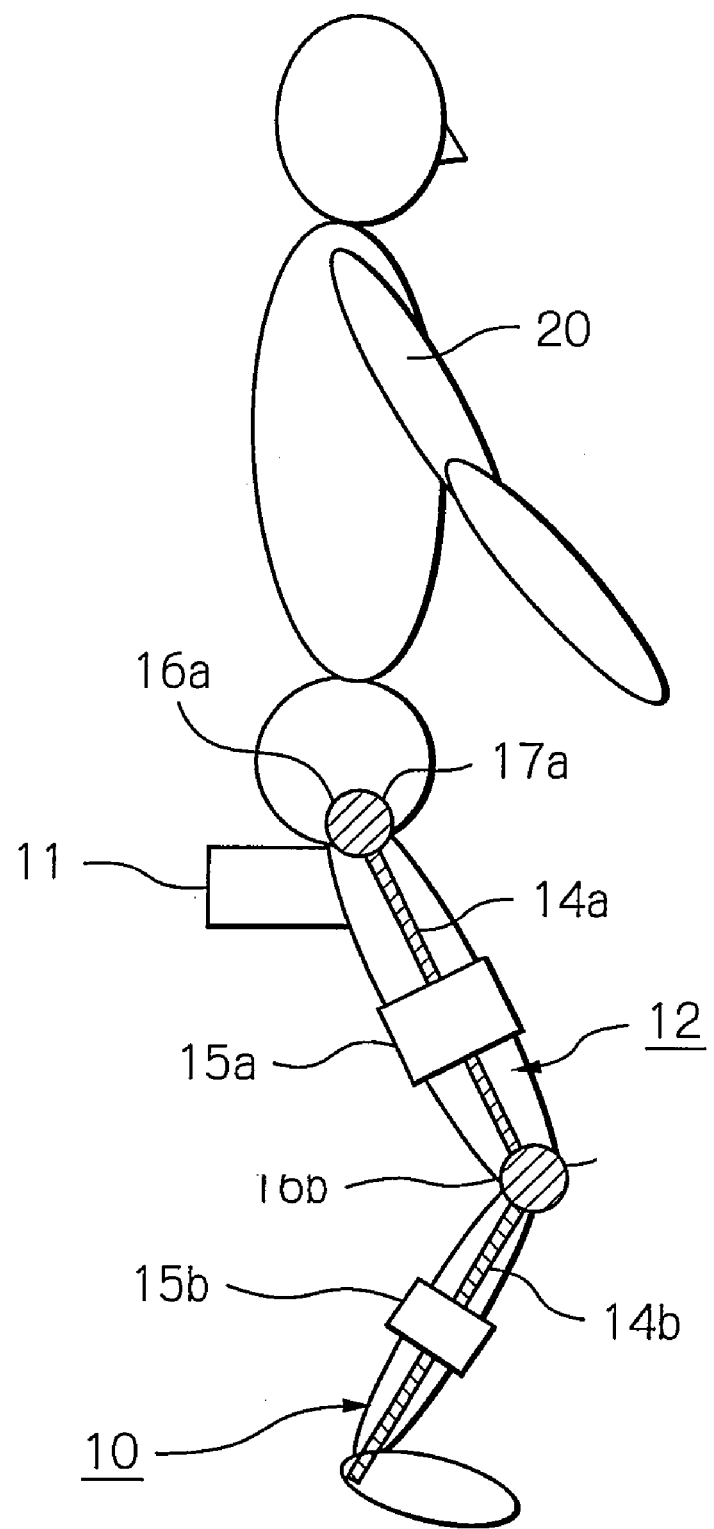
FIG. 1 is a side elevation schematically showing a use environment of a resistance training apparatus in accordance with the present invention.

With reference to the accompanying drawings, a preferred embodiment of the present invention will now be described in detail. First with reference to FIG. 3, the reference numeral 20 denotes a user, or test subject, in the present embodiment. The user, or testee, has his or her muscular force evaluated using the present resistance-based muscular force evaluation system. Initially, by way of giving the background information of the resistance-based muscular force evaluation system, the bi-articular link mechanism of the limbs of a human body will be described insofar as such description is necessary for understanding the present invention.

Figure 6:
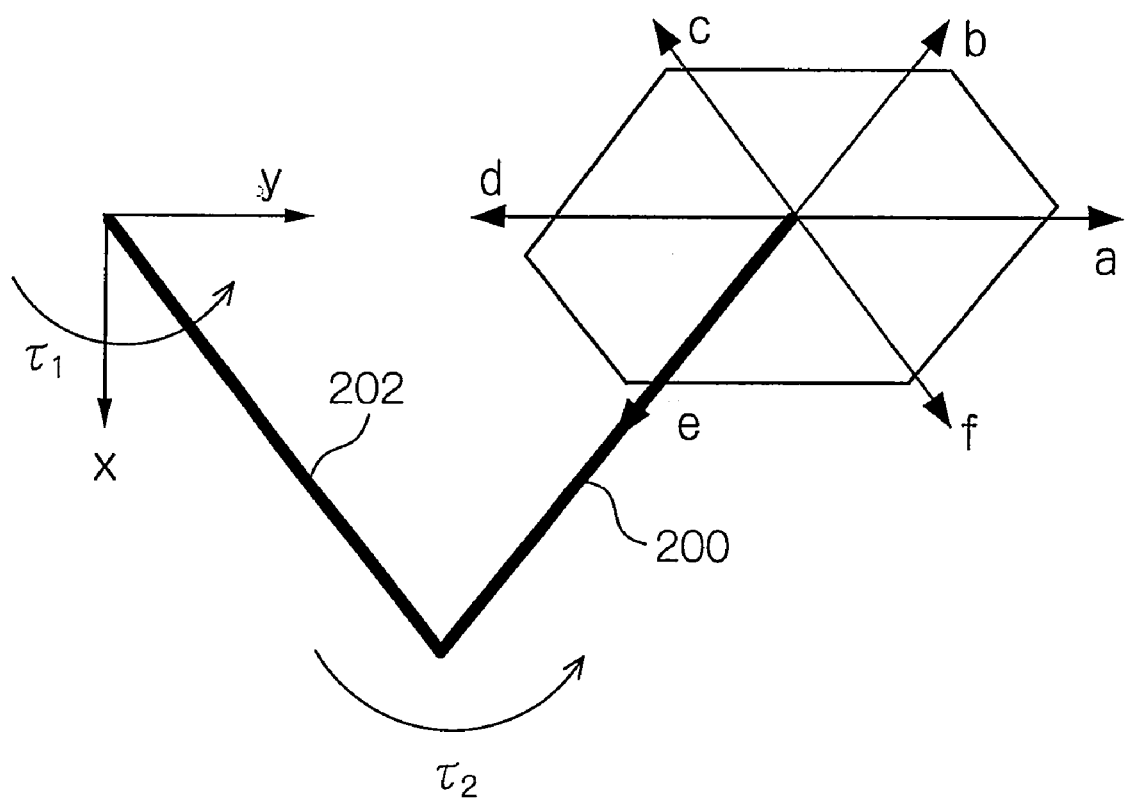
FIGS. 6 and 7 show the output distribution of the force at the distal end of the link system and the torques at the joint axles, respectively, according to the preferred embodiment.
Figure 7:
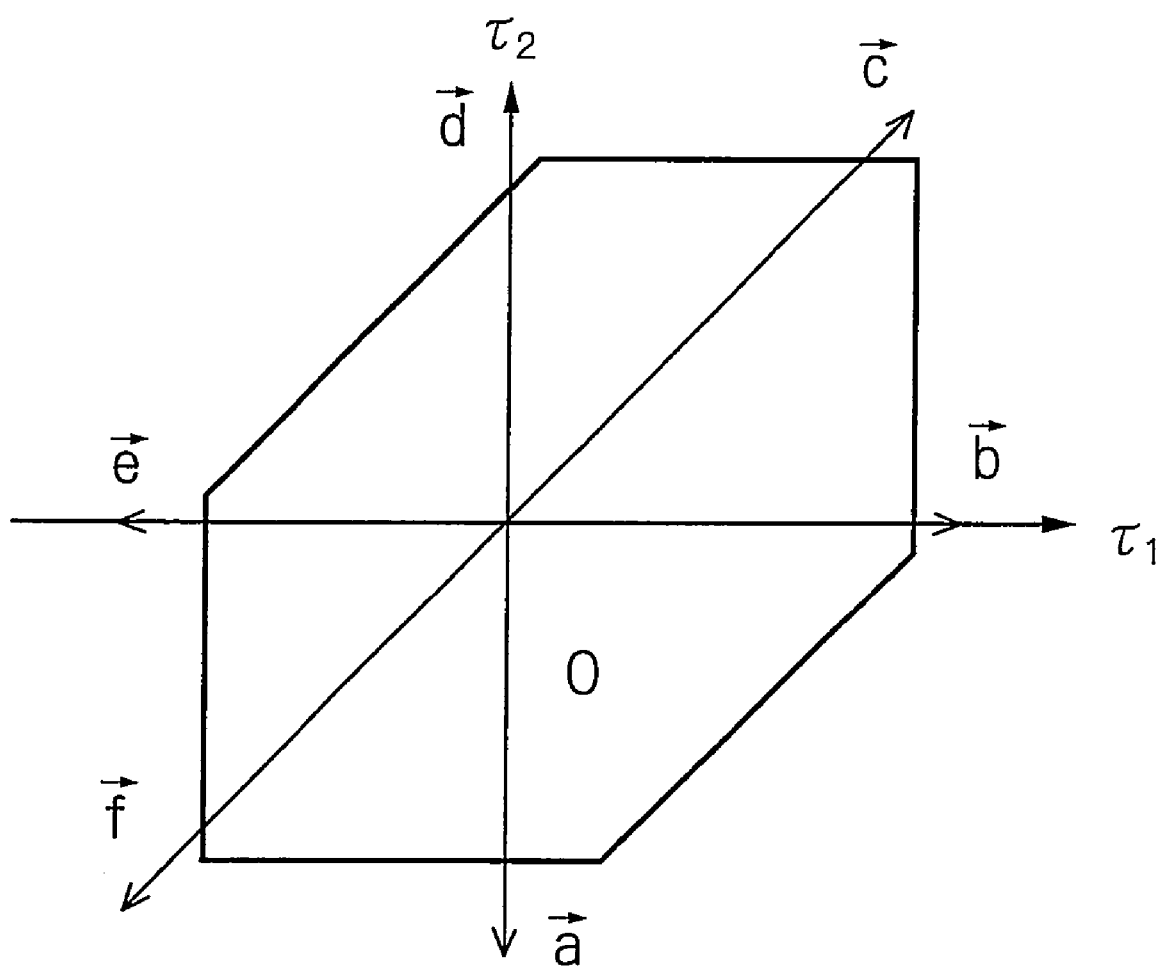

In a known manner, the limbs, that is, four limbs, of the human body have bi-articular muscles, which act in concert with the mono-articular muscles, each operating on a sole joint, to control at its distal end an output which may be represented by hexagonally-shaped output distribution shown in FIGS. 6 and 7, as disclosed for example in T. Fujikawa et al., "Coordinate Activities of a Group of Mono-articular Muscles and a Group of Bi-articular Muscles in Upper Limbs, Acting in Antagonism to One Another, and Analysis of Control Functions thereof by a Mechanical Model", Biomechanisms 13, The Society of Biomechanisms, pp. 181-191, 1996. There is also known a method for evaluating the force of muscles based on functions, in accordance with hexagonally-shaped output distribution characteristics, as disclosed for example also in Japanese '272 publication stated earlier.

Figure 3:
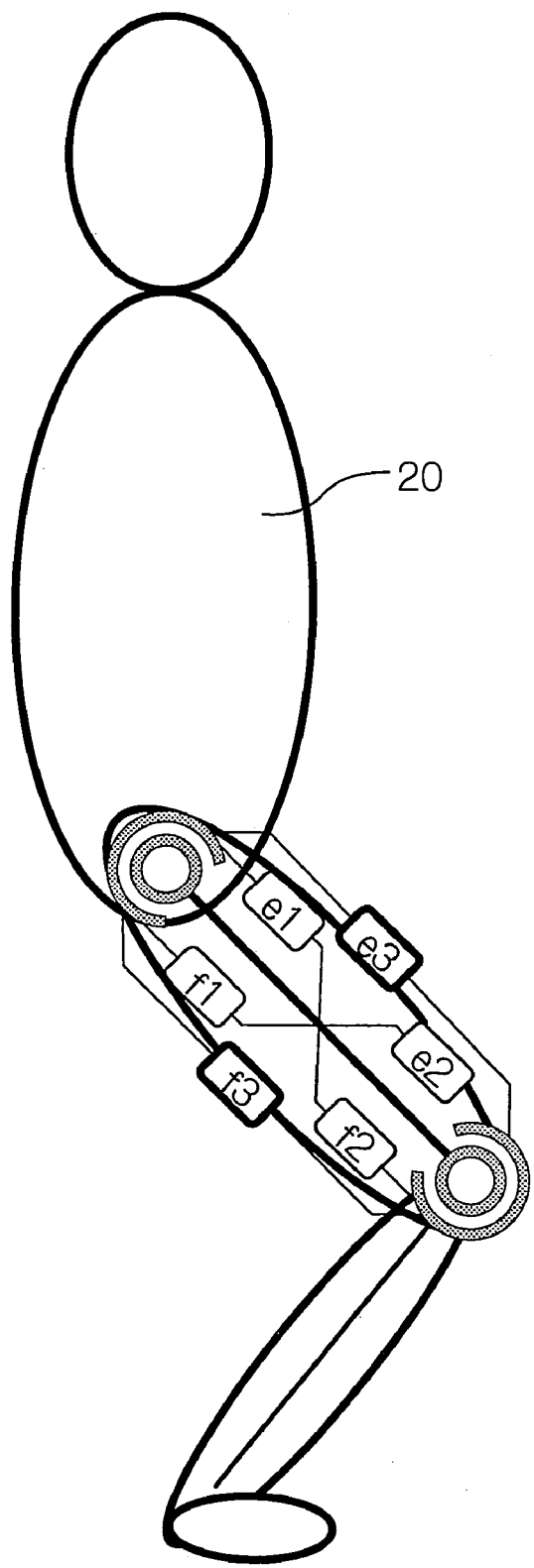
FIG. 3 schematically shows groups of muscles of a user's limb for use in describing a preferred embodiment of the present invention.
Figure 4:
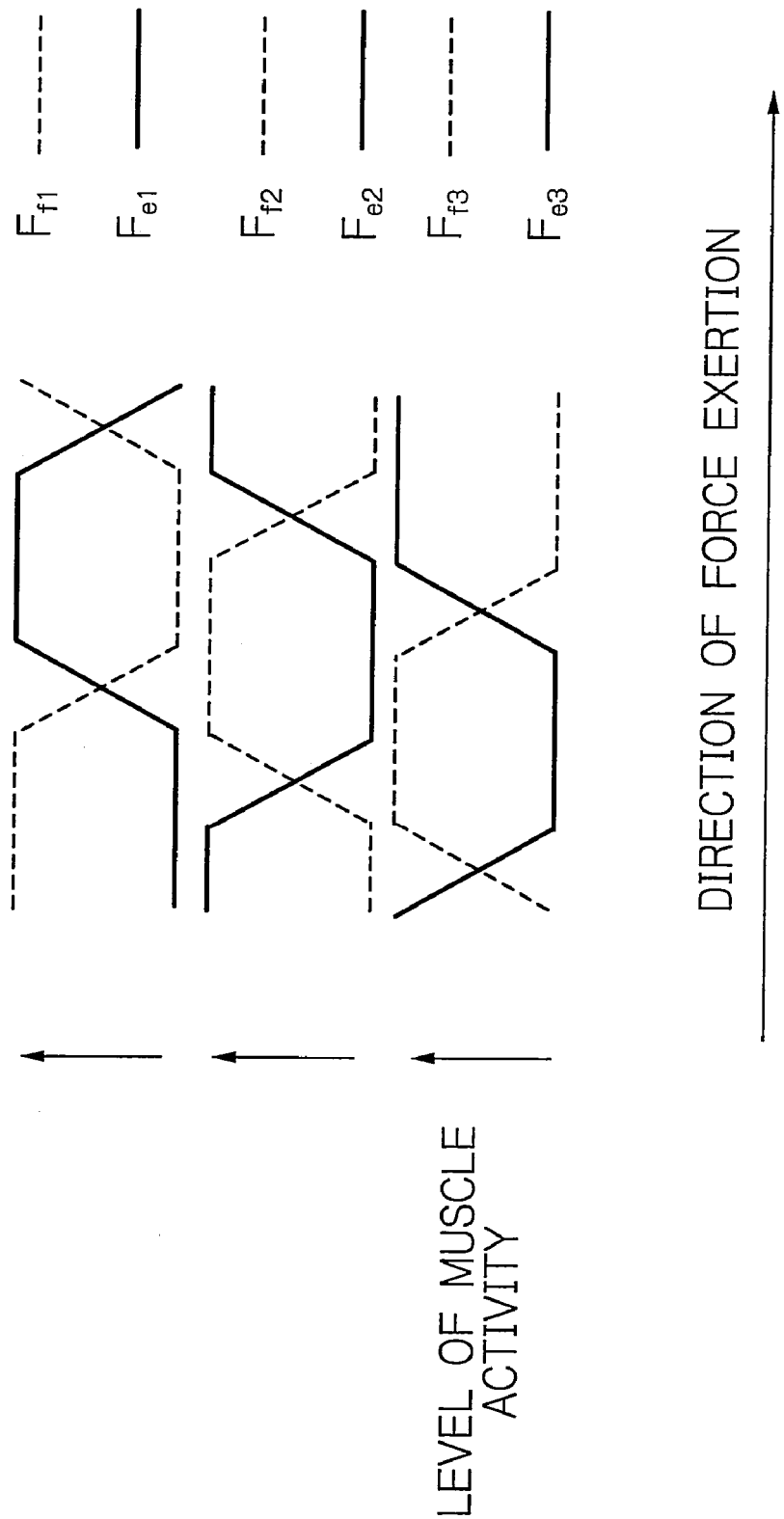
FIG. 4 schematically shows the degree or pattern of activities of the muscles of the user's limb in the preferred embodiment.

The output characteristics at the distal ends of the four limbs, disclosed in both of the prior art documents, will now be described insofar as such a description is necessary for understanding the present invention. Each of the upper and lower limbs of a human body may be represented, in an exercise movement in a bi-dimensional plane including a first and a second joint and a distal end of the pertinent system, i.e. the link system of a bi-articular link mechanism of the testee, or test subject, by three pairs of muscles, i.e. six muscles, taking account of the functions of the muscles. As shown in FIG. 4, these muscles are an antagonistic mono-articular muscle pair (f1, e1) around the first joint, an antagonistic mono-articular muscle pair (f2, e2) around the second joint, and an antagonistic bi-articular muscle pair (f3, e3), lying astride the first and second joints. The muscles are termed function-based muscles of praxis. The muscles shown by way of example in FIG. 3 are a group of muscles acting on a hip and a knee joint of the lower limb of the user 20.

The mono-articular muscle refers to a muscle acting only on a sole joint. The mono-articular muscle of the upper limb may be exemplified by the anterior or posterior part of a deltoid of a shoulder joint, brachia muscle of an elbow joint and the caput lateralis (outer head) of the triceps of the upper arm. The mono-articular muscle of the lower limb may be exemplified by musculus gluteus maximus, waist joint, caput breve (short head) of biceps of thigh and vastus lateralis of the knee joint. Specifically, the bi-articular muscles of the upper limb may be exemplified by the biceps of the upper arm and the caput longum (long head) of the triceps of the upper arm, while that of the lower limb may be exemplified by ham strings or the straight muscle of thigh.

An output displayed at the distal end of a bi-articular link system of the upper and lower limbs of the human body, that is, at the joint of the wrist part of a hand for the upper limb and at the ankle joint for the lower limb, and the direction of the output, are controlled by coordinate activities of the function-based muscles of praxis, namely the aforementioned three pairs of muscles, or the six muscles. If the force is exerted with the maximum effort in respective directions at the distal end of the link system, the function-based muscles of praxis, namely the aforementioned three pairs of muscles, are alternately contracted, depending on the directions of force exertion, as shown in FIG. 4. In this figure, F denotes the magnitude of the force of the joint muscles indicated by the suffixes.

Figure 5:
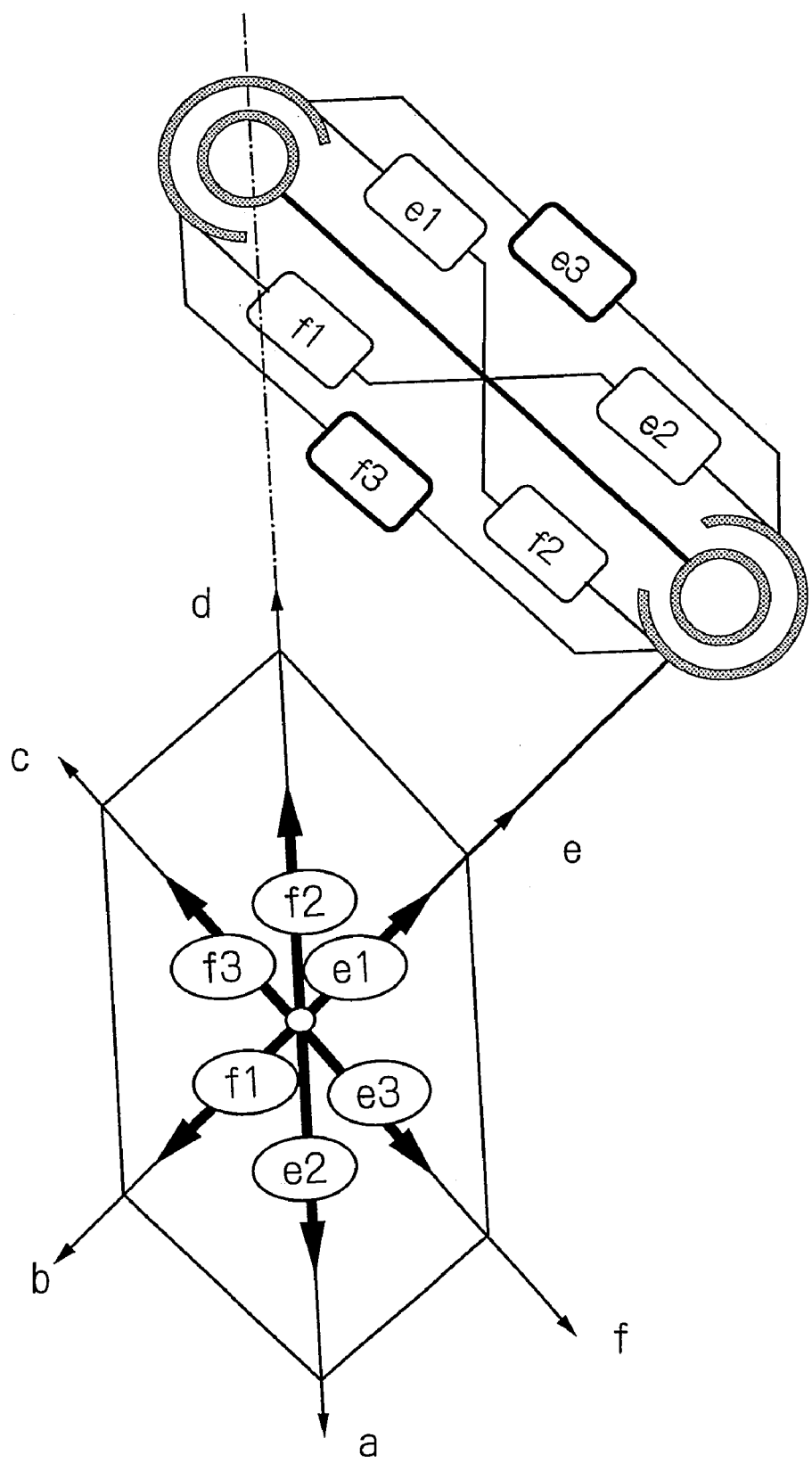
FIG. 5 schematically shows characteristics of the output distribution of the muscles of the user's limb in the preferred embodiment.

The directions of the force generated at the distal ends of the limb due to the contractile force displayed by the three pairs of function-based muscles of praxis at the distal ends of the limbs are indicated in FIG. 5. More specifically, hexagonally-shaped maximum output distribution characteristics are exhibited by forces combined under the coordinate control in accordance with the alternating patterns shown in FIG. 4.

It is characteristic that the sides of the hexagon of the maximum output distribution characteristics are parallel to the first and second links and a straight line interconnecting the first joint with the distal end of the link system. Hence, the hexagonal shape differs with the positions of the limbs. Even though the contractile forces of the muscles remain constant so that the torque generated in each joint is not changed, the force generated at the distal end of the limb of the human body is changed in direction and magnitude in dependent upon the torques at the joint axles, depending on the positions of the upper or lower limb.

Figure 2:
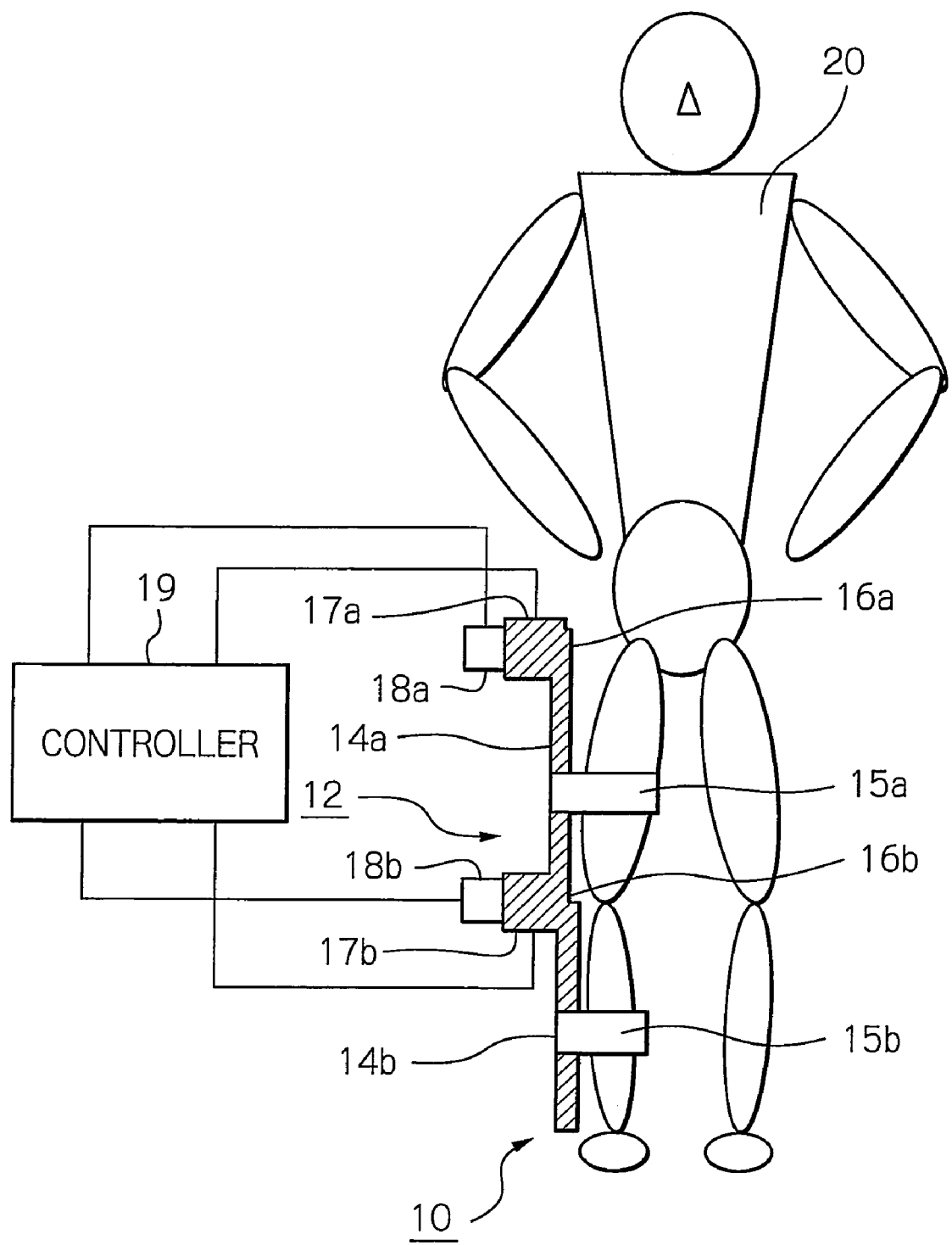
FIG. 2 is a front view schematically showing the use environment of the resistance training apparatus shown in FIG. 1.

The constitution of the apparatus for resistance-based muscular force evaluation 10 of the present embodiment will now be described. FIGS. 1 and 2, which schematically show the constitution of the illustrative embodiment of the present invention, are a side and a front view, respectively, of the apparatus for resistance-based muscular force evaluation.

The resistance-based muscular force evaluation apparatus 10 of the instant embodiment provides for most effective resistance-based muscular force evaluation with the aforementioned output characteristics of the limbs of the human being taken into account. Referring to FIG. 1, the resistance-based muscular force evaluation apparatus 10 is made up of a saddle 11, on which sits a user, i.e. test subject, 20, a robot arm 12, a controller 19 for controlling the robot arm 12, and an operational console, not shown, for allowing the user or subject 20 to input his or her intention of having his or her muscular force evaluated. The robot arm 12 is attached to and extends along, the limb of the user 20. Although the lower limb is taken here for description, the system may apply for the upper limb as well.

The robot arm 12 is made up of two links, that is, a first link 14a for a thigh and a second link 14b for a lower leg, and hence has its degree of freedom equal two. The first link 14a and the second link 14b are each provided with a slide mechanism for adjusting the link length. For resistance-based muscular force evaluation, the first and second links are adjusted so as to be almost or substantially equal in length to the thigh and the foot of the user 20, respectively, and are fastened to the thigh and the leg using a first fastener 15a and a second fastener 15b, respectively. The first link 14a and the second link 14b may sometimes be referred collectively to as a link 14. The first fastener 15a and the second fastener 15b may also sometimes be referred collectively to as a fastener 15.

The robot arm 12 is worn by the user 20 when he or she is seated on the saddle 11. At this time, a first joint axle 16a of the robot arm 12 is brought into register with the hip joint of the user 20, and a second joint axle 16b of the robot arm 12 is brought into register with the axis of his or her knee joint.

To the first joint axle 16a and the second joint axle 16b, connected are a first servo motor 17a and a second servo motor 17b, respectively. There is also provided an absolute type of encoders serving as angular sensors 18a and 18b for sensing the joint angles. The first joint axle 16a and the second joint axle 16b may sometimes be referred to collectively as a joint axle 16. The first servo motor 17a and the second servo motor 17b may also sometimes be referred to collectively as a servo motor 17. The servo motor 17 operates as a driving source for the joint and generates a torque for causing the joint axle to rotate. The torque generated by the servo motor 17 is controlled by the aforementioned controller 19. The torques generated at the joint axles of the robot arm 12 may be recorded by a recorder, not shown, connected to the controller 19.

To the controller 19 are connected a display unit, which may be a cathode-ray tube (CRT), a liquid crystal display or electro-luminescence display device, not shown, and an output device such as a printer. The output device is for use in displaying or printing a hexagonal diagram plotting an output distribution prepared, as will be described later on, or informing the user 20 of the directions in which the force is to be applied, for example.

Figure 8:
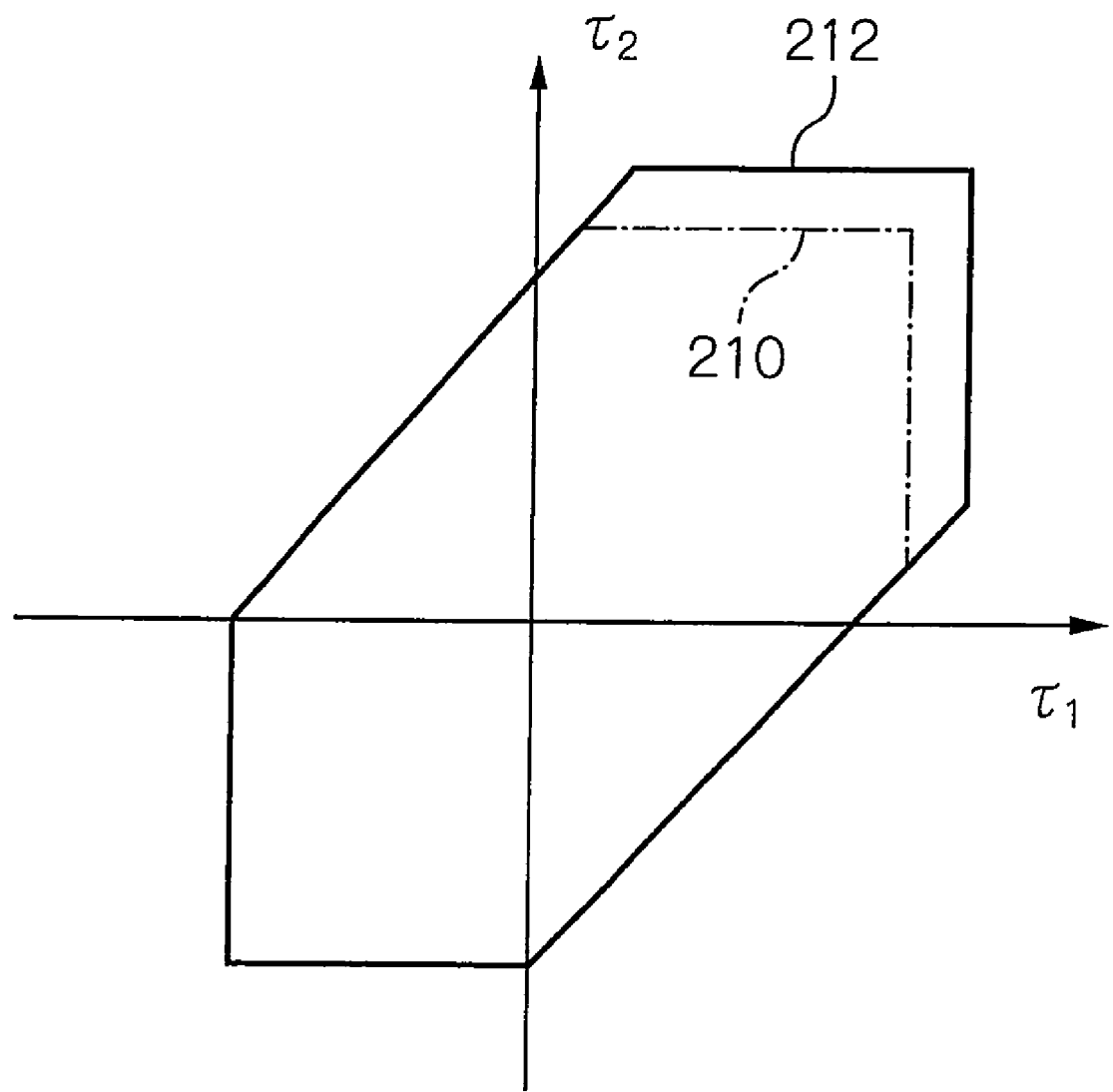
FIG. 8 shows a change in output distribution of the torques at the joint axles before and after training according to the preferred embodiment.

The operation of the above-described muscular force evaluating apparatus 10 will now be described in detail. FIGS. 6 and 7 comparatively show the distribution of the force output at the distal end of the link system in the preferred embodiment of the invention and the output distribution of the torques at the joint axles, respectively. FIG. 8 shows a change in output distribution of the torques at the joint axles before and after training in the preferred embodiment.

The output distribution of the force, exerted at the distal end of the link system, more specifically, at the joint of the wrist part of the hand for the upper limb or at the ankle joint for the lower limb, is varied with the joint angle of the link system. Thus, with the present embodiment, an output distribution diagram of the torques at the joint axles which is shown in FIG. 7 is taken up for scrutiny in which the axial torques at the first joint ($\tau 1$) and the second joint ($\tau 2$) which could be generated at the respective joints simultaneously are plotted on the abscissa and the ordinate, respectively.

According to the theory of the function-based muscles of praxis, the output distribution of the torques at the joint axles is hexagonally shaped, like the distribution of the force output at the distal end of the link system, such as shown in FIG. 6. The output distribution of the torques at the joint axles, shown in FIG. 7, is correlated with the output distribution of the force at the distal end of the link system shown in FIG. 6.

The correlation between the two hexagons, shown in FIGS. 6 and 7, will now be described. FIG. 6 corresponds to output distribution characteristics taught in the Japanese '272 publication indicated earlier. In the hexagon shown in FIG. 6, the two sides parallel to a second rod, that is, the second link 200, are not changed in moment about the second joint. Hence, these sides are equivalent to straight lines which are parallel to the $\tau 1$ axis, where $\tau 2$=constant, in the diagram of the output distribution of the torques at the joint axles. In a similar manner, in the hexagon shown in FIG. 6, the two sides parallel to the straight line interconnecting the first joint and the distal end of the link system, are not changed in moment about the first joint. Hence, in the diagram of output distribution of the torques at the joint axles, the above two sides are equivalent to straight lines parallel to the $\tau 2$ axis where $\tau 1$=constant.

Among the sides of the hexagon, shown in FIG. 6, the two sides parallel to the first rod, that is, to the first link 202, will now be taken up for scrutiny. When the changes in the force from one of the ends to the opposite ends of these sides are scrutinized, the direction of the changes in force is parallel to the direction of the first link 202, such that these sides may be thought of as affording the same changes in torque at the first and second joints. Hence, these two sides are equivalent to straight lines parallel to a line for $\tau 1 = \tau 2$.

If it is possible to measure the output distribution of the torques at the joint axles, such as shown as the diagram in FIG. 7, it is also possible to obtain the diagram for the output distribution at the distal end of the link for optional joint angles.

In order to evaluate the force of the individual function-based muscles of praxis, this force may be estimated by specifying the cross-sectional area, less the fat part, of the antagonistic bi-articular muscle pair, as taught in the Japanese '272 publication.

Further in the resistance-based muscular force evaluation apparatus 10, in order to obtain a diagram for output distribution of the torques at the joint axles, the user 20 exerts the force with the maximum effort in various directions with the robot arm 12 attached along the lower limb of the user 20. In this state, the force exerted by the user 20 with maximum effort is recorded as the torques at the joint axles. In this case, the user 20 is indicated, e.g. visually of the direction of the force to be exerted so as to appropriately exert the force. Since the robot arm 12 generates the force of reaction for the user 20, as the torque at the joint axis is controlled to prevent the joint angle from being changed, the torque at the joint axle when the joint angle is not changed is recorded as the torque, as exerted at the joint axle by the user 20.

The values of the so recorded torques at the joint axles are plotted on the τ1-τ2 coordinate plane, shown in FIG. 8, as the torque values that can be generated simultaneously at the two joint axles. The hexagon of the smallest size is drawn which contains the set of all plots, with its two sides running parallel to the τ1-axis, with its other two sides running parallel to the τ2-axis and with its remaining two sides running parallel to a line of τ2=τ1, and is used as a diagram of output distribution of the torques at the joint axles. A hexagon 210 formed using the muscular force resistance-based muscular force evaluation apparatus 10 before the user 20 proceeds to training and a hexagon 212 formed using the muscular force resistance-based evaluation apparatus 10 after the user 20 has finished the training may be displayed on the same viewing screen, as shown in FIG. 8, to help the user comprehend the changes in his or her muscular force before and after the training.

The user may also perform training using the muscular force resistance-based evaluation apparatus 10. In performing the training, the user 20 operates the operational console, not shown, for the resistance-based muscular force evaluation apparatus 10, to input or set up a training menu or schedule. The training menu is input as the user enters the output direction in which lies the distal end of the limb the user wants to train, and the magnitude of the training load, based on the hexagon of distribution characteristics of the maximum output indicated for example in FIG. 5.

For example, it is supposed that the user 20 intends to increase the jump distance of a standing broad jump, and hence to augment the output at the distal end in a direction b in the hexagon shown in FIG. 5. The user 20 then selects the direction b as the output direction for training, while inputting the magnitude of the training load. It is seen from the alternating pattern of the three pairs of muscles, shown in FIG. 4, that the muscles that are in operation when the user 20 exerts the force in the direction b are f1 (group of hip joint mono-articular flexers), e2 (group of knee joint mono-articular flexers) and f3 (group of bi-articular flexers for thigh).

For augmenting the output at the distal end, in the direction b, it is sufficient to train the group of three muscles, that is, f1, e2 and f3. Hence, in the resistance-based muscular force evaluation apparatus 10, the torques generated by the first servo motor 17a and the second servo motor 17b, associated with the hip joint and the knee joint, respectively, when the above group of three muscles is in operation, are increased in the opposite directions, either progressively or stepwise, up to the magnitude of the training load as input by the user 20. The user 20 then exerts the force to oppose to the torques generated by the evaluation apparatus 10 to maintain the state of the predetermined or intended muscle output to train his or her muscular force.

Since the resistance-based muscular force evaluation apparatus 10 exerts a constant torque as a load to the user 20, he or she may perform the isometric training provided that he or she makes an endeavor not to change the position of the distal end of his or her limb (ankle in the above example). Moreover, since the load applied to the muscle is not changed even if the user 20 is changed in position during training, he or she may perform the isotonic training.

Thus, in the present embodiment, if the test subject, or person, 20 is desirous to evaluate his or her muscular force, changed resultantly from some training, that is, evaluate the difference in muscular force brought about by the training, it is possible to evaluate what changes have been caused in the muscular force, from changes in the hexagonal shape, representing the output distribution of the torque at the joint axles, without the necessity of specifying the muscular force of the individual function-based muscles of praxis.

If, as a result of some training, the output distribution of the torque at the joint axles has changed as shown in FIG. 8, it may be evaluated that the favorable effect similar to that brought about by the increased force of the muscles of praxis f3 has been achieved.

The output distribution of the force at the distal end of the link system is varied with the length and angle of each link. However, the output distribution of the torques at the joint axles is varied only with the output of the muscles of praxis. Thus, if it is desired to obtain the diagram for the output distribution of the torques at the joint axles, the information on the position of the user 20 is unneeded.

That is, with the use of the diagram for the output distribution of the torques at the joint axles, the magnitudes of the muscular force of the muscles of praxis may be compared despite difference in angle of the joints at the time of measurement.

An alternative embodiment of the present invention will now be described. Like parts or components are designated by the same reference numerals and a repetitive description thereof will be dispensed with. A description of the operation and advantages which are the same as the illustrative embodiment described above will also be dispensed with.

The resistance-based muscular force evaluation apparatus 10 in accordance with the present alternative embodiment is adapted to employ control of stiffness characteristics at the distal end of the link, taught by co-pending U.S. patent application Ser. No. 11/878,709 filed prior to the present patent application and assigned to the same assignee. The present alternative embodiment may otherwise be the same as the preferred embodiment and hence a repetitive corresponding description will be dispended with.

Figure 9:
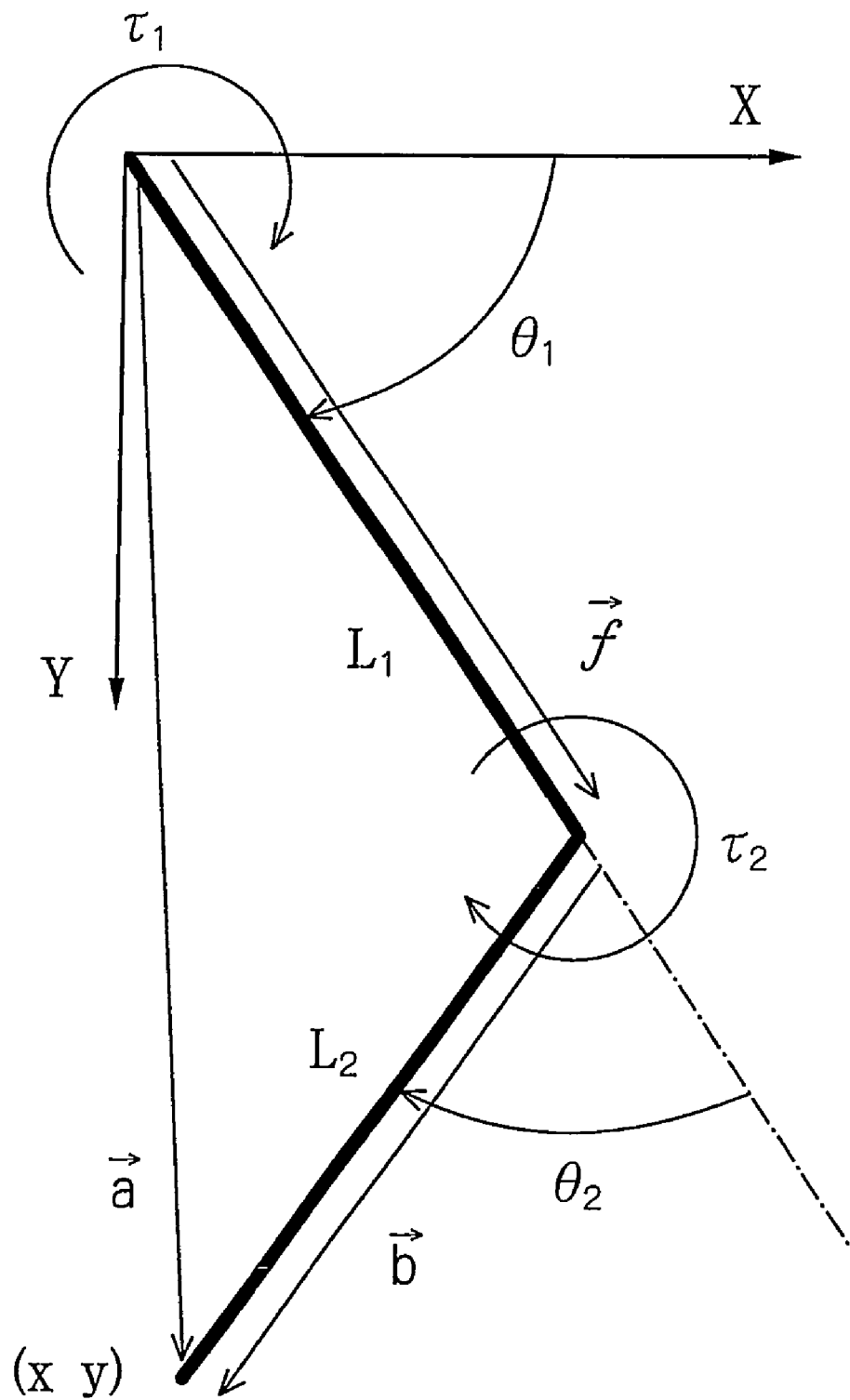
FIG. 9 is a chart useful for understanding how to align the load direction with the eigenvector of stiffness characteristics in an alternative embodiment of the present invention.

The operation of the resistance-based muscular force evaluation apparatus 10 in the alternative embodiment will now be described in detail. FIG. 9 schematically illustrates how the direction of the load may be brought into register with the eigenvector of stiffness characteristics in the present alternative embodiment.

The resistance-based muscular force evaluation apparatus 10 is controlled so that the torque generated by a joint driving source provided on each joint will be equal to a value calculated by the following expression (1)

$$\begin{pmatrix} \tau_{a1} \\ \tau_{a2} \end{pmatrix} = \begin{pmatrix} \tau_{u1} \\ \tau_{u2} \end{pmatrix} - \begin{pmatrix} \kappa_{11} & \kappa_{12} \\ \kappa_{21} & \kappa_{22} \end{pmatrix} \begin{pmatrix} \delta_1 \\ \delta_2 \end{pmatrix} \qquad (1)$$

based on joint angles as measured by a joint angular sensor 18a of 18b provided on each joint. This reproduces characteristics substantially equivalent to stiffness characteristics and output characteristics at the distal ends of the four limbs of a human body as clarified by the aforementioned T. Fujikawa, et al.

With the present alternative embodiment, it is possible to afford elliptical stiffness characteristics to the distal end of the robot arm 12 of the resistance-based muscular force evaluation apparatus 10. The user 20 may be guided to perform proper measurement by the direction of the force being measured for the user 20, as displayed by taking advantage of the stiffness characteristics.

The stiffness characteristics may be represented in the form of relationship of the joint torque with the angle of displacement by a matrix of the following expression (2)

$$\begin{pmatrix} \kappa_{11} & \kappa_{12} \\ \kappa_{21} & \kappa_{22} \end{pmatrix} \quad (2)$$

and may be represented by an ellipse in the case of bi-articular link.

The transverse and conjugate axes of the ellipse are substantially coincident with the direction of the eigenvector of the matrix and perpendicular to each other. The modulus of elasticity along the transverse or conjugate axis of the ellipse is coincident with the eigenvalue for the eigenvector. With the robot arm 12 of the muscular force resistance-based evaluation apparatus 10, the eigenvalue and the eigenvector may be set to optional values.

In this case, the load direction is determined by the training menu as input by the user 20. Thus, the modulus of elasticity is set so that the modulus of elasticity in the direction of the load will be smaller than that in the direction perpendicular to the load direction, i.e. anisotropic. The controller 19 exercises control to generate the joint torque responsive to the displacement of the joint angle from outside based on the so set stiffness characteristics. If the user 20 exerts the force to afford the angular displacement to the robot arm 12, then a load torque is generated by the robot arm 12 in dependence upon the angular displacement.

The direction in which the user 20 is desirous to perform training is such a direction in which the modulus of elasticity is low and displacement is more liable to be caused than in any other direction. Hence, the user 20 is able to recognize the direction in which he or she is to exert the force as being a direction in which he or she may move his or her body limb more readily.

It will now be described how the load direction may be brought into register with the eigenvector of the stiffness characteristics. Referring to FIG. 9, a vector â, beginning at a hip joint and terminating at a foot joint, and a vector b̂, beginning at a knee joint and terminating at the foot joint, as the directions in a work space for measurement, are represented as base vectors. In the description, a vector is denoted with a hat "^" following a letter. The direction in the hexagon shown in FIGS. 6 and 7, in which the force is to be exerted, is defined by the following expression (3)

$$\vec{p}_s = \alpha \vec{a} + \beta \vec{b} \quad (3)$$

If the Jacobian determinant at the distal end of the bi-articular arm mechanism is labeled J, the direction perpendicular to the direction $p_s$ may be represented by the following expression (4)

$$\vec{q}_s \; // \; J \begin{pmatrix} \alpha \\ \beta \end{pmatrix} \quad (4)$$

Additionally, the following expression (5) is valid, $$\begin{aligned} KP &= K(\vec{p}_s \; \vec{q}_s) \\ &= (K\vec{p}_s \; K\vec{q}_s) \\ &= P \begin{pmatrix} \lambda_1 & 0 \\ 0 & \lambda_2 \end{pmatrix} \end{aligned} \quad (5)$$

where $\lambda_1$ and $\lambda_2$ denote the modulus of elasticity in a direction $\vec{P}_s$ and that in a direction $\vec{q}_s$, respectively.

Hence, the relationship between the joint torque and displacement of the distal end of the bi-articular arm mechanism may be represented by the following expression (6)

$$K = P \begin{pmatrix} \lambda_1 & 0 \\ 0 & \lambda_2 \end{pmatrix} P^{-1} \quad (6)$$

If the above relationship is rewritten into the relationship between the joint torque and the displacement of the joint angle, with the use of the relationship between the displacement of the distal end of the bi-articular arm mechanism and the displacement of the joint angle, then the following expression (7) will be obtained $$G = \begin{pmatrix} g_{11} & g_{12} \\ g_{21} & g_{22} \end{pmatrix} = J^T P \begin{pmatrix} \lambda_1 & 0 \\ 0 & \lambda_2 \end{pmatrix} P^{-1} J \quad (7)$$

Since J is the Jacobian determinant, the above relationship is the function of the joint angle. Hence, in order to find out the elements of the matrix J, actual joint angles are measured by joint angle detection units provided at the joints of the robot arm 12.

By the above expressions, the torques at the joint axles to be generated by the robot arm 12 when the robot arm 12 is displaced from the reference point are calculated. The torques at the joint axles of the robot arm 12 are then controlled, with the so calculated values of the torques at the joint axles as target values, to arrive at desired stiffness characteristics.

In the above expression (3), between the three pairs of muscles, if the ratio of the scalars (α, β) pertinent to the vectors â and b̂ is equal, then the ratio of the muscular forces exerted by the three pairs of muscles of praxis is also equal. If the ratio of the muscular forces, exerted by the three pairs of the muscles of praxis, is equal, then the directions in the τ1-τ2 plane are also equal.

In order to measure the output distribution of the torques at the joint axles, the user 20 has to exert the force with the maximum effort in plural directions. Thus, to indicate the user of the direction of the force to be exerted to measure the output distribution of the torques at the joint axles, control of stiffness characteristics is used. More specifically, the modulus of elasticity for the direction in which the user 20 desirably exerts the force is lowered, while that for the direction perpendicular thereto is raised, thereby indicating the user 20 of the direction based on the difference in the magnitudes of the force of reaction generated when the user 20 moves his or her leg with a certain effort. Conversely, in order to indicate the direction for the user 20, the modulus of elasticity for the direction in which the user 20 desirably exerts the force and that for the direction perpendicular thereto to may be raised and lowered, respectively, depending on the liking of the particular user 20.

Thus, in the present alternative embodiment, the hexagon of the diagram plotting the output distribution of the torques at the joint axles is not dependent on the angles at the joint axles, and hence the user 20 may vary his or her position during measurement. Thus, the user 20 may be indicated of the direction in which to exert the muscular force, based on his or her pressure sensation, that is, based on the hard or soft force of reaction as felt by the user 20 against his or her force exerted.

As described above, the illustrative embodiments are directed to the resistance-based evaluation of the muscular force of the muscles of praxis of the lower limb. Since the muscles of the upper limb are similar to those of the lower limb in having both of the mono-articular and the bi-articular muscles, the force of the muscles of praxis may be evaluated of the upper limb in a similar manner using the apparatus for evaluating the muscular force.

The entire disclosure of Japanese patent application No. 2007-048511 filed on Feb. 28, 2007, including the specification, claims, accompanying drawings and abstract of the disclosure is incorporated herein by reference in its entirety.

While the present invention has been described with reference to the particular illustrative embodiments, it is not to be restricted by the embodiments. It is to be appreciated that those skilled in the art can change or modify the embodiments without departing from the scope and spirit of the present invention.

What is claimed is:

1. A resistance-based muscular force evaluation apparatus comprising:
   a saddle on which a test subject sits;
   a robot arm adjustable to a length of an upper limb or a lower limb of the test subject, and having a first joint and a second joint;
   a fastener for securing said robot arm to the upper limb or the lower limb of the test subject;
   an angular sensor for sensing joint angles at the first and second joints of said robot arm; and
   a controller for measuring and controlling a first torque at the first joint and a second torque at the second joint of said robot arm generated simultaneously by a coordinated action of the antagonistic mono-articular muscles and antagonistic bi-articular muscles of the test subject, and evaluating a change in muscular force of the test subject based on a change in a hexagonal diagram of output distribution formulated on a plane formed by two axes corresponding to the first torque and the second torque.

2. The apparatus in accordance with claim 1, wherein the first torque and the second torque are measured when a force exerted at a distal end of said robot arm is brought into register with a force exerted by the distal end of a link system of a bi-articular link mechanism of the test subject.

3. A method for resistance-based muscular force evaluation of a bi-articular link mechanism of a test subject, wherein the bi-articular link mechanism includes a set of antagonistic mono-articular muscles about a first joint and a set of antagonistic mono-articular muscles about a second joint, both of the sets of muscles giving rise to effective movement in a plane including the first and second joints and a distal end of the articular link mechanism, and a set of antagonistic bi-articular muscles astride the first and second joints, said method comprising:

providing a robot arm including a first link and a second link, respectively connecting opposite ends of the first link to a first joint and a second joint of a test subject, connecting a first end of the second link to the second joint and forming a distal end of the robot arm at a second end;
measuring a first torque at the first joint and a second torque at the second joint generated simultaneously by a coordinated action of the antagonistic mono-articular muscles and antagonistic bi-articular muscles of the test subject;
formulating a hexagonal diagram of output distribution on a plane formed by two axes corresponding to the first torque and the second torque; and
evaluating a change in muscular force of the bi-articular link mechanism of the test subject based on a change in the diagram.

4. The method in accordance with claim 3, wherein the torques at the first joint and the second joint are measured when the force exerted at the distal end of the robot arm is brought into register with the force exerted by the distal end of the mechanism.

5. A resistance-based muscular force evaluation system for a bi-articular link mechanism of a test subject, the bi-articular link mechanism including a set of antagonistic mono-articular muscles about a first joint and a set of antagonistic mono-articular muscles about a second joint, both of the sets of muscles producing an exercise movement in a plane including the first and second joints and a distal end of the articular link mechanism, and a set of antagonistic bi-articular muscles astride the first and second joints, said system comprising:
   a first link having opposite ends respectively connected to a first joint and a second joint of a test subject; and
   a second link having a first end connected to the second joint and a second end forming a distal end of the link mechanism,
   wherein a first torque at the first joint and a second torque at the second joint are generated simultaneously by a coordinated action of the antagonistic mono-articular muscles and antagonistic bi-articular muscles being measured,
   a hexagonal diagram of output distribution is formulated on a plane formed by two axes corresponding to the first torque and the second torque, and
   a change in muscular force of a link mechanism of the test subject is evaluated based on a change the diagram.

6. The system in accordance with claim 5, further comprising:
   a saddle on which a test subject sits;
   a robot arm adjustable to a length of an upper limb or a lower limb of the test subject, and having a first joint and a second joint;
   a fastener for securing said robot arm to the upper limb or lower limb of the test subject;
   an angular sensor for sensing joint angles at the first and second joints of said robot arm; and
   a controller for controlling a first torque at a first joint or a second torque at a second joint of said robot arm, the first torque and the second torque being measured when the muscular force exerted at a distal end of said robot arm is brought into register with the force exerted by the distal end of the link mechanism of the test subject.

7. The apparatus in accordance with claim 1, wherein the distal end of said robot arm exhibits elasticity, said controller varying the elasticity with respect to a direction of manual force applied by the test subject to indicate the direction in which the test subject is to exert the manual force to allow measurement of the muscular force.

8. The method in accordance with claim 3, further comprising measuring the muscular force of the bi-articular link mechanism of the test subject based on the diagram.

9. The system in accordance with claim 5, wherein the muscular force of the link mechanism of the test subject is measured based on the diagram.

* * * * *